United States Patent [19]
Conlan

[11] Patent Number: 5,573,013
[45] Date of Patent: *Nov. 12, 1996

[54] METHOD OF MONITORING BODY MOVEMENTS USING ACTIVITY MONITORING APPARATUS

[75] Inventor: Robert W. Conlan, Niceville, Fla.

[73] Assignee: Precision Control Design, Inc., Fort Walton Beach, Fla.

[*] Notice: The portion of the term of this patent subsequent to Jun. 17, 2011, has been disclaimed.

[21] Appl. No.: 479,822

[22] Filed: Jun. 7, 1995

Related U.S. Application Data

[63] Continuation of Ser. No. 341,316, Nov. 16, 1994, abandoned, which is a continuation of Ser. No. 38,629, Mar. 29, 1993, abandoned, which is a continuation of Ser. No. 716,853, Jun. 17, 1991, Pat. No. 5,197,489.

[51] Int. Cl.⁶ .................................................. A61B 5/103
[52] U.S. Cl. .................................................. 128/782
[58] Field of Search ........................... 128/782, 774, 128/721, 722, 670, 671, 687, 713, 714; 340/573

[56] References Cited

U.S. PATENT DOCUMENTS

| | | | |
|---|---|---|---|
| 3,807,388 | 4/1974 | Orr et al. | 128/690 |
| 4,088,139 | 5/1978 | Auerbach | 128/419 PT |
| 4,117,834 | 10/1978 | McPartland et al. | 128/782 |
| 4,202,350 | 5/1980 | Walton | 128/690 |
| 4,353,375 | 10/1982 | Colbrun et al. | 128/782 |
| 4,425,921 | 1/1984 | Fujisaki et al. | 128/690 |
| 4,428,378 | 1/1984 | Anderson et al. | 128/419 PG |
| 4,819,652 | 4/1989 | Micco | 128/661.09 |
| 4,830,021 | 5/1989 | Thornton | 128/707 |
| 4,945,916 | 8/1990 | Kretschmer et al. | 128/671 |
| 4,989,612 | 2/1991 | Fore | 128/721 |
| 5,010,887 | 4/1991 | Thornander | 128/696 |
| 5,010,893 | 4/1991 | Sholder | 128/782 |
| 5,025,791 | 6/1991 | Niwa | 128/670 |
| 5,031,614 | 7/1991 | Alt | 128/419 OPG |
| 5,036,856 | 8/1991 | Thornton | 128/670 |
| 5,044,365 | 9/1991 | Webb et al. | 128/419 PG |
| 5,074,303 | 12/1991 | Hauck | 128/419 PG |
| 5,197,489 | 3/1993 | Conlan | 128/782 |

OTHER PUBLICATIONS

Experimental Prototype (AM-16) Block Diagram (date unknown).

Redmond, D. and Hegge, F., "Observations on the design and specification of a wrist–worn human activity monitoring system" Behavior Res. Methods, Instruments & Computer, (1985).

*Primary Examiner*—Guy V. Tucker
*Attorney, Agent, or Firm*—Lockwood, Alex, Fitzgibbon & Cummings

[57] ABSTRACT

An activity monitor adapted to be worn on the non-dominant wrist of a subject includes a bimorphous beam motion sensor. The output signal of the sensor is amplified in an amplifier circuit having a selectable amplification factor, and filtered by highpass and lowpass filter circuits having individually selectable cut-off frequencies to obtain an analog signal for processing having a bandpass and amplitude characteristic corresponding to a particular body activity under observation. A control and processing circuit within the monitor includes a microprocessor which responds to either resident internal operating instructions or to externally supplied operating instructions, or to designated data signal parameters, to provide configuration control signals to the amplifier and filter circuits, and processing of the collected data, appropriate to the particular activity being monitored. The processed data is digitally stored in an internal memory for subsequent transfer through a data port to an associated computer for display or further processing.

7 Claims, 8 Drawing Sheets

$$y = y_0 \sec\left(\pi \frac{T}{E}\right)$$

where:
y = Signal Amplitude
$y_0$ = Threshold Amplitude
T = Time Above Threshold
E = Epoch $$y = y_0 \sec\left(\pi \frac{T_T}{E}\right)$$

where:
$T_T = 4T$

METHOD OF MONITORING BODY MOVEMENTS USING ACTIVITY MONITORING APPARATUS

This application is a continuation of application Ser. No. 08/341,316, filed Nov. 16, 1994, now abandoned, which is a continuation of application Ser. No. 08/038,629, filed Mar. 29, 1993, now abandoned, which is a continuation of application Ser. No. 716,853, filed Jun. 17, 1991, now U.S. Pat. No. 5,197,489.

BACKGROUND OF THE INVENTION

The subject invention relates to apparatus and methods for monitoring activity of the human body. More particularly, the invention relates to apparatus, systems and methods by which the occurrence and length of certain types of body movements which form activity phenomenon can be selectively observed and accurately quantified.

A human subject engages in a wide range of body movements. Such movements can range from the voluntary and visually perceptible—such as the movement of legs, arms and head, to the involuntary and visually imperceptible, such as the slight changes in elevation of skin caused by the rhythmic pulsations of blood and breathing.

The observation of body movement can provide much information useful to physicians and researchers. For example, by observing a subject's movements, the occurrence and length of natural phenomenon, such as wakefulness, rest and sleep can be determined. By observing the nature of a subject's movement, the occurrence and severity of disorders and the effects of drugs or other therapy can be assessed. In many cases quantification of the subject's movement is preferred so that the movement pattern of one subject can be compared with the movement pattern of others.

Direct visual observations of body movement are labor intensive, time consuming and tedious. Moreover, direct visual observations provide only a limited range of qualitative information, such as subjective descriptions of a subject's visually perceptible movements. Little, if any, quantification in readily comparable values, such as degree, strength, and/or violence of a subject's activity, and no information, either qualitative or quantitative, of a subject's visually imperceptible movements is obtained. Furthermore, the value of qualitative information obtained by directly observing a subject is subject to question as such observations themselves may cause the subject to become conscious of and thereby alter his or her movements.

Activity monitors have been developed for observing and quantifying certain aspects of movement without the involvement of an observer. However, such monitors had disadvantages which limited their usefulness. For example, such prior monitors were typically of a size which interfered with free movement of the subject, and typically had either little or no internal memory and/or little or no data processing capabilities. In order that data produced by many of these activity monitors could be stored and/or processed it was necessary to connect the monitors through cables to external data storage and processing devices. Tethering the monitor in this way to an external device also tethered the subject to the device, thereby restricting the subject's movement and biasing the results.

In those prior activity monitors which had internal memory, saturation of the memory occurred when the subject engaged in activity which produced a volume of data that, for the period of time over which the subject was being monitored, exceeded the capacity of the memory.

This problem was aggravated because prior activity monitors were not selectively configurable to collect data only for a particular activity, so that unusable or irrelevant data was often allowed to occupy memory space along with usable data. Prior monitors did not have the capability to be reconfigured according to preset instructions and/or in response to the data collected by the monitor.

Prior monitors typically utilized sensors to detect body movement which, because of the need to suppress harmonics and other artifacts from the limited memory, lacked the sensitivity to detect small scale, visually imperceptible movements such as those caused by breathing, the beat of the heart, and the flow of blood.

A demand therefore exists for an activity monitor and method by which the activity of a subject, even that activity which includes movements that are not necessarily visually perceptible, can be selectively observed and accurately quantified. The present invention satisfies this demand.

Accordingly, it is a general object of the present invention is to provide an improved apparatus, system and methods for selectively observing and accurately quantifying certain aspects of the motion of a subject.

An object of the present invention is to provide an activity monitor having a size and construction such that the monitor may be conveniently worn on the subject.

Another object of the present invention is to provide an activity monitor which can collect data regarding a subject's activity automatically and according to instructions initialized in the monitor.

Another object of the present invention is to provide an activity monitor having a memory in which operating instructions and collected data are stored.

Another object of the present invention is to provide an activity monitor with which data regarding a subject's movement can be processed automatically and according to instructions initialized in the monitor.

Another object of the present invention is to provide an activity monitor wherein the type of data collected and the processing of the data by the monitor can be automatically changed.

SUMMARY OF THE INVENTION

The present invention is directed to an activity monitor and methods by which both visually perceptible and visually imperceptible movement can be selectively observed and accurately quantified.

The apparatus includes an activity monitor, or actigraph, having a size, shape and construction that allows the monitor to be worn on the surface of the skin of a subject and which functions reliably and without restriction of the subject's movement. One preferred embodiment of the monitor of the present invention is configured for wearing on a subject's non-dominant wrist. The monitor may be configured to be worn on other parts of a subject's body as well.

In particular, the activity monitor of the present invention includes a movement sensor by which the full range of a subject's movement, even that which is visually imperceptible, can be detected. A preferred sensor is a cantilever piezoelectric bimorph beam. The use of a bimorph beam as a sensor is advantageous in that it provides high sensitivity and operates without requiring any operating power, such as from a battery, thereby conserving this generally limited resource. Furthermore, such a sensor operates in the absence of a gravitational field thereby expanding the applications in which the monitor can be utilized.

The bimorph beam in response to an applied force produces a signal whose frequency varies according to the movement to which the monitor is subjected. When the monitor is secured adjacent to the surface of the skin of a subject, such as on the subject's non-dominant wrist, the monitor produces signals having frequencies ranging from approximately 0.16 hertz to 9 hertz. Within this frequency range, certain activities of the subject produce frequencies falling within certain specific narrow frequency ranges. For example, breathing produces a signal having a frequency range of 0.2 to 1 hertz, the beat of the heart produces a signal having a range of 2 to 3 hertz, and the typical night time activity of a subject produces a signal having a range between 0.2 and 3 hertz. Disorders, such as tremor activity, typically produce a signal having a range of 2 to 9 hertz.

So that such specific frequency ranges among the wide range of frequencies which a subject's many movements produce can be selectively observed and quantified, the activity monitor includes signal processing means which amplify, shape and filter the signal produced by the sensor.

In particular, so that a low amplitude signal, such as those produced by breathing and heart beats, can be isolated for later processing, the activity monitor includes signal conditioning means in the form of a motion signal amplifier having an amplification factor selectable by an applied configuration control signal, and a highpass filter circuit having a threshold selectable by another applied configuration signal below which motion sensor signals are greatly attenuated. This is advantageous in that it allows observations to be made of a subject both during a high activity period, when a relatively high amplitude high frequency signal is produced by the sensor, and during a low activity period, such as during the night, when the subject is typically producing a relatively low amplitude and low frequency signal.

To eliminate DC drift in the motion signal amplifier the signal processing means preferably include a drift compensation circuit which compares the dc level of the amplified motion signal developed by the amplifier with a fixed dc reference voltage to develop a drift corrected voltage at the motion detector which nulls out any drift.

To eliminate artifacts present in the sensor output signal, such as those caused by the natural resonance of the motion sensor, and to obtain in conjunction with the highpass filter a desired frequency spectrum for analysis and quantification, the activity monitor includes a low pass filter circuit having a threshold frequency selectable by applied configuration signals.

The activity monitor further includes an analog-to-digital converter which samples the analog signal developed by the motion sensor, after processing by the amplifier, high-pass filter and low-pass filter, and passes the resultant digital values to internal memory means in the monitor for storage and later retrieval.

The activity monitor also includes a window detector which compares the voltage level of the processed motion signal to upper and lower voltage thresholds selectable by an applied configuration signal, and provides an activity count each time the signal voltage level crosses the thresholds. Preferably, the signal voltage level is compared to both a high threshold voltage level and a low threshold voltage level which are symmetrically positioned opposite the regulated reference voltage. Preferably, the amount by which the upper and lower thresholds differ exceeds the amount of noise which the system normally generates so that counts generated by the detector are caused by variations in the motion detector output signal and not by monitor noise.

The activity monitor further includes a temporary internal memory for recording the activity counts generated by the activity detector over a selectable observation period, or epoch. At the end of the epoch, the total number of events occurring during the epoch is stored, and the temporary memory is erased for use during the next epoch. Advantageously, the epoch time period is selected according to the type of activity to which the observation is directed.. For example, because a subject engages in generally less movement while asleep, the epoch used during such an observation period can be generally of greater duration than that, for example, used when a subject is monitored while awake. A selectable epoch period avoids the memory saturation problem that prior monitors had in collecting data for periods of time inappropriate to a particular type of movement.

The activity monitor also includes an internal microprocessor having resident software by which the configuration of the various circuits of the monitor are controlled. The microprocessor is preferably capable of powering up and shutting down the processing circuits at selected times to conserve battery power.

The microprocessor has associated with it memory in which software to control the monitor components is resident and in which data obtained from the operation of the monitor is stored. Specifically, the memory includes a read-only memory (ROM) which contains instructions to operate the monitor. Preferably, the ROM includes an operating system by which the monitor's signal processing components can be initially configured so that, for example, certain aspects of a subject's movement can be initially observed, from which the monitor's signal processing components can be reconfigured so that other aspects of a subject's movement can be observed, and by which the data that is collected is stored.

Advantageously, to provide an activity monitor which is fully adaptable and which can be altered to collect data regarding activity patterns not initially envisioned, the monitor memory includes a random-access memory (RAM) for storing instructions, for example, different from those stored in the ROM. Advantageously, the monitor can operate off either, or a combination of those instructions stored in the ROM or in the RAM.

Communication between the activity monitor and, for example, a personal computer, with which the data obtained by the monitor be stored, evaluated, and further processed, and from which new instructions to be stored in the monitor RAM can be prepared, is facilitated by an interface unit providing electrical connections between the monitor and the computer. To this end, the interface unit preferably includes a receptacle for receiving the monitor, and the monitor is provided with an electrical connector on the surface of its housing which engages a complementary connector in the receptacle.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

DESCRIPTION OF THE PREFERRED EMBODIMENT

Figure 1:
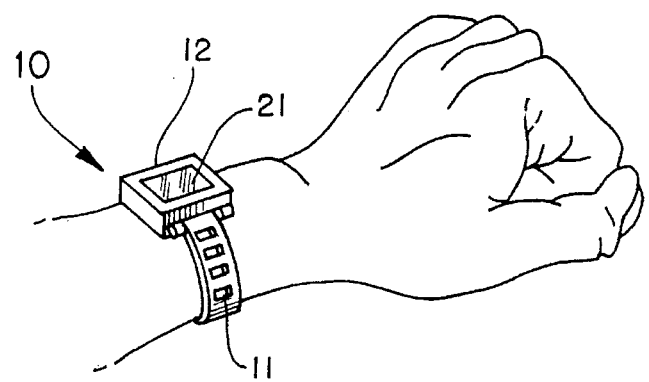
FIG. 1 is a perspective view of a wrist-mounted activity monitor constructed in accordance with the invention as worn on the wrist of a subject.
Figure 2:
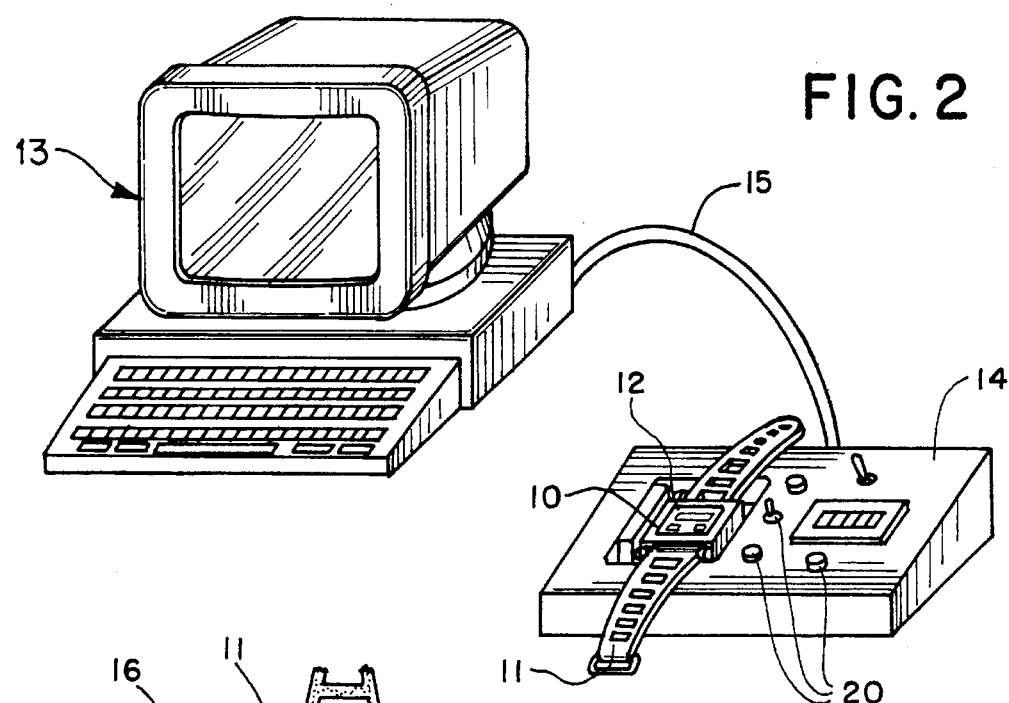
FIG. 2 is an activity monitoring system including a computer, interface and wrist-mounted activity monitor constructed in accordance with the invention.

Referring to the Figures, and particularly to FIGS. 1 and 2, a wrist-mounted activity monitor or actigraph 10 constructed in accordance with the invention may be similarly shaped and sized to a wrist-watch, having a flexible band 11 securing a generally rectangular housing 12 against the skin surface of a subject being monitored. Typically, in this form the monitor is mounted on the non-dominant wrist, the activity of which has been found to correlate with body activity, muscle movement and brain waves.

Figure 3:
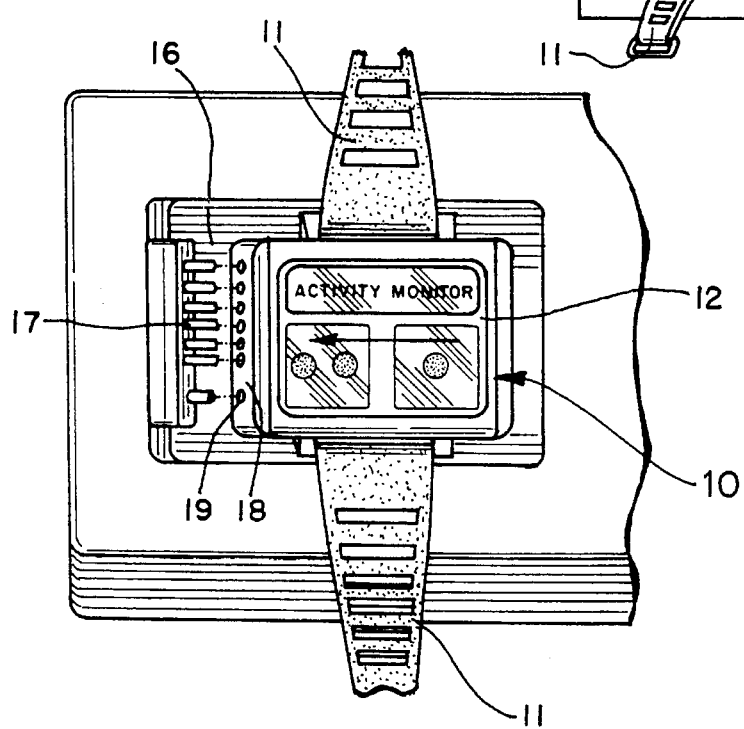
FIG. 3 is an enlarged perspective view of a portion of the interface unit shown in FIG. 2 showing the positioning of the wrist-mounted activity monitor therein.

In use, the activity monitor 10 is worn by the subject for a predetermined collection period which may extend over one or more days. Data collected by the monitor over the collection period is downloaded at the end of the period to a personal computer 13 which, except for containing necessary software for accomplishing the down-loading of data from the monitor and the uploading of operating instructions to the monitor, may be entirely conventional in construction and operation. Communication between the activity monitor 10 and computer 13 is facilitated by an interface unit 14, which is connected to a data port of computer 13 by means of a conventional RS-232 cable 15 or the like. The interface unit 14 preferably includes a receptacle 16 (FIG. 3) on its top surface dimensioned to receive the monitor housing 12. An electrical connector 17 located along one side of receptacle 16 engages a connector 18 on housing 12 when the monitor is seated within the receptacle. With this arrangement the monitor can be quickly and conveniently installed and removed from interface unit 14. A plurality of controls 20 on the top surface of interface unit 14 assist the operator in accomplishing the downloading and uploading functions.

Activity monitor 10, personal computer 13 and interface unit 14 together comprise a system for collecting and analyzing human activity data. Depending on the particular software resident in personal computer 13 a wide variety of written reports and displays may be generated from the data collected by the monitor.

Figure 4:
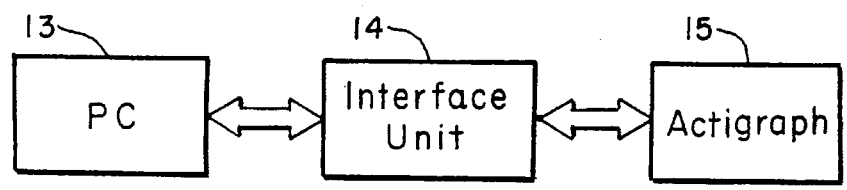
FIG. 4 is a functional block diagram showing the principal components of the activity monitoring system of FIG. 2.

In this regard, and with reference to FIG. 4, data is exchanged between personal computer 13 and interface unit 14 in both directions, and between interface unit 14 and activity monitor 10 in both directions. This provides complete flexibility in that necessary operating instructions may be provided to monitor 10 through interface unit 14 from personal computer 13. When the monitor is removed from interface unit 14, these resident instructions control the operation of the monitor in a subsequent data collection assignment. As will be seen, a number of operating parameters in the monitor can be configured for either an entire data collection period, or for portions of a data collection period, or for single epochs, providing activity data and an activity monitor of optimum utility.

Figure 5:
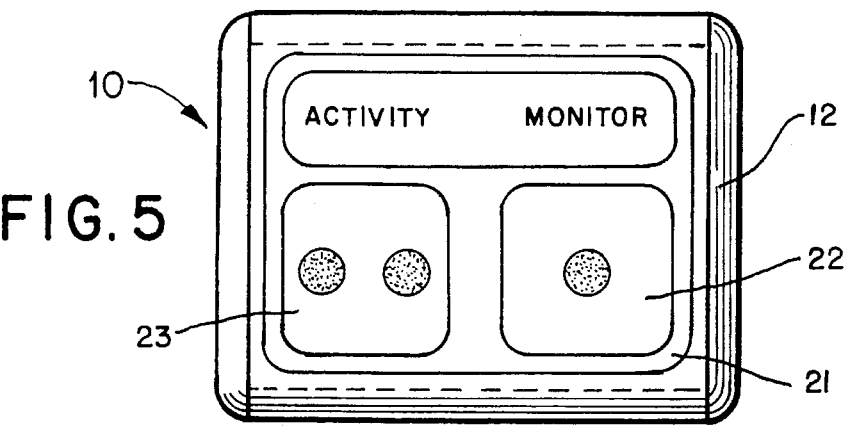
FIG. 5 is an enlarged plan view of the control panel of the wrist-mounted activity monitor of FIGS. 1–3.

Referring to FIG. 5, the top surface of activity monitor 10 includes a pair of user-input pushbutton switches 22 and 23. These switches, which are preferably membrane type switches, allow the subject to indicate the occurrence of a particular event. For example, upon the occurrence of dizziness or pain, the subject may be instructed to depress one of the push button switches to cause that occurrence to be recorded in the internal memory of the monitor. To enable these switches to be readily identified, the right switch may be one color, such as red, may be provided with a single raised dimple for tactile feedback, and may be accompanied by a single audible beep. The left pushbutton switch 22 may be provided with two raised dimples, may be another color, such as green, and may cause two audible beeps when actuated.

Figure 6:
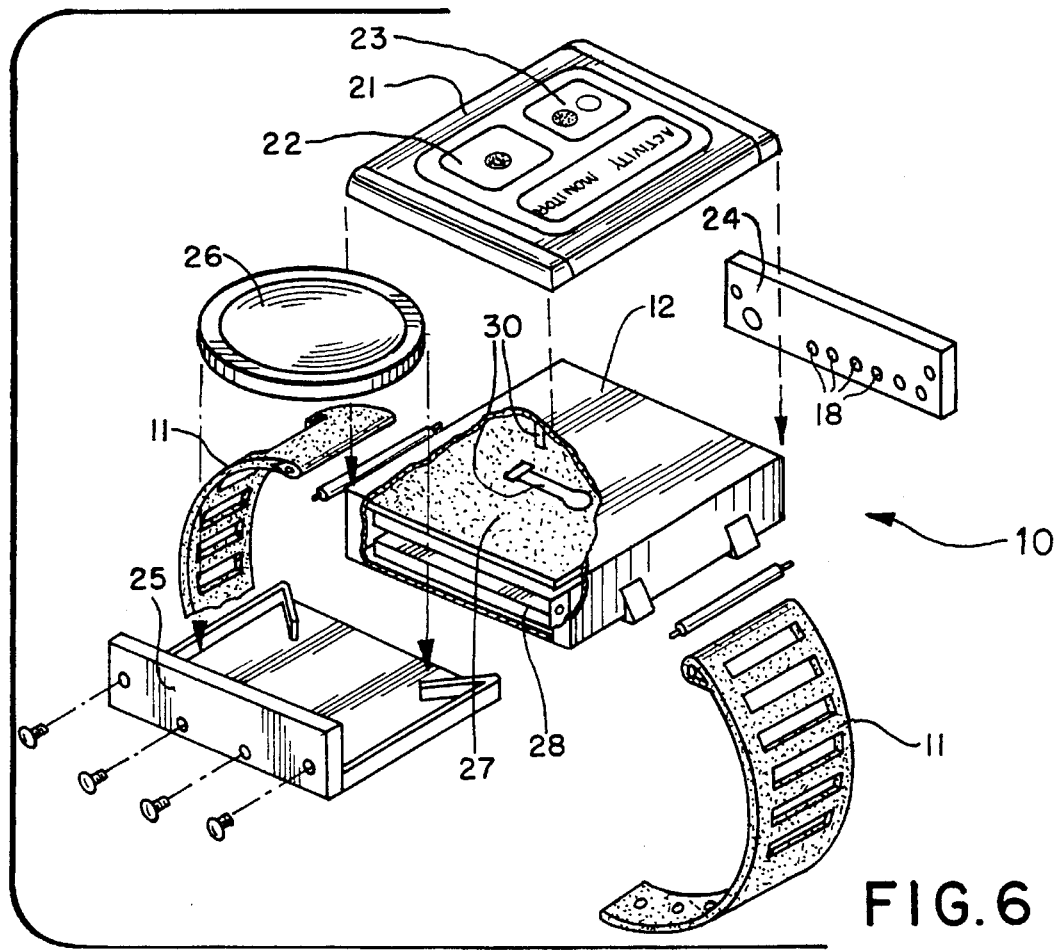
FIG. 6 is an exploded perspective view of the wrist-mounted activity monitor showing certain principal components thereof.

Referring to FIG. 6, the housing 12 of activity monitor 10 is seen to include a side panel 24 on which electrical connector 18 is positioned for engaging the electrical connector 17 of receptacle 16. The other side of housing 12 includes a sliding tray assembly 25 within which a coin-type battery cell 26 is mounted for insertion into housing 12. Within housing 12 a first circuit board 27 and a second parallel-spaced circuit board 28 provide mounting and connection means for a major portion of the circuitry of the monitor, and also provide mounting means for motion sensing means in the form of a cantilever piezoelectric bimorph beam motion sensor 30.

Figure 7:
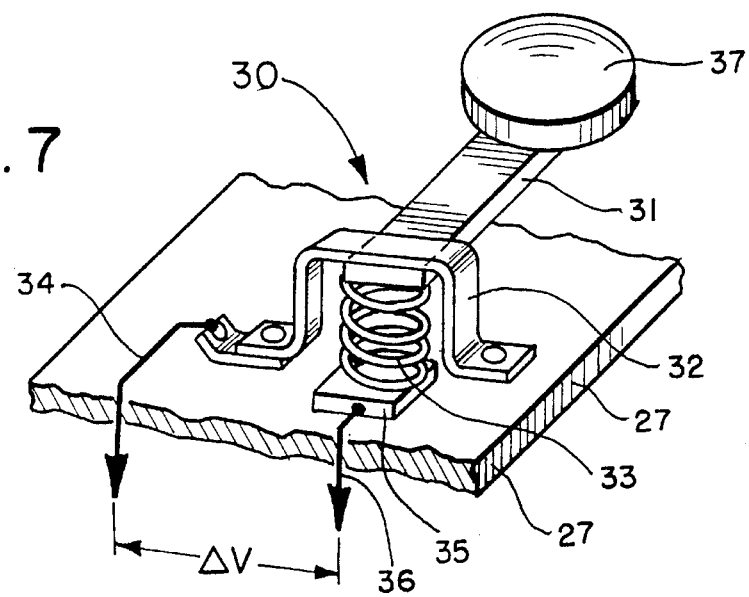
FIG. 7 is an enlarged perspective view of the piezoelectric bimorph beam motion detector utilized in the activity monitor of FIGS. 1–3.

Referring to FIG. 7, motion sensor 30 is seen to comprise a bimorph beam 31 fixedly positioned relative to circuit board 27 at one end by a metallic clamp 32 and compression contact 33. The compression contact 33 forces one face of beam 31 against clamp 32, completing one electrical connection to the beam through a conductor 34. The other electrical connection to beam 31 is established through compression contact 33, which bears against the other face of the beam and a metallic pad 35 on circuit board 27 to which a conductor 36 is connected. Thus, the bimorph beam is electrically connected on opposite faces to the circuitry of the monitor by mounting means which fixedly position the connected end relative to circuit board 27. The distal end of beam 31 may be fitted with a proof mass 37 to impart desired electro-mechanical characteristics to the bimorph beam assembly 30. This method of making connections to the bimorph beam has the advantage of avoiding solder connections to the beam, and their attendant cracking or deterioration with time.

Figure 8:
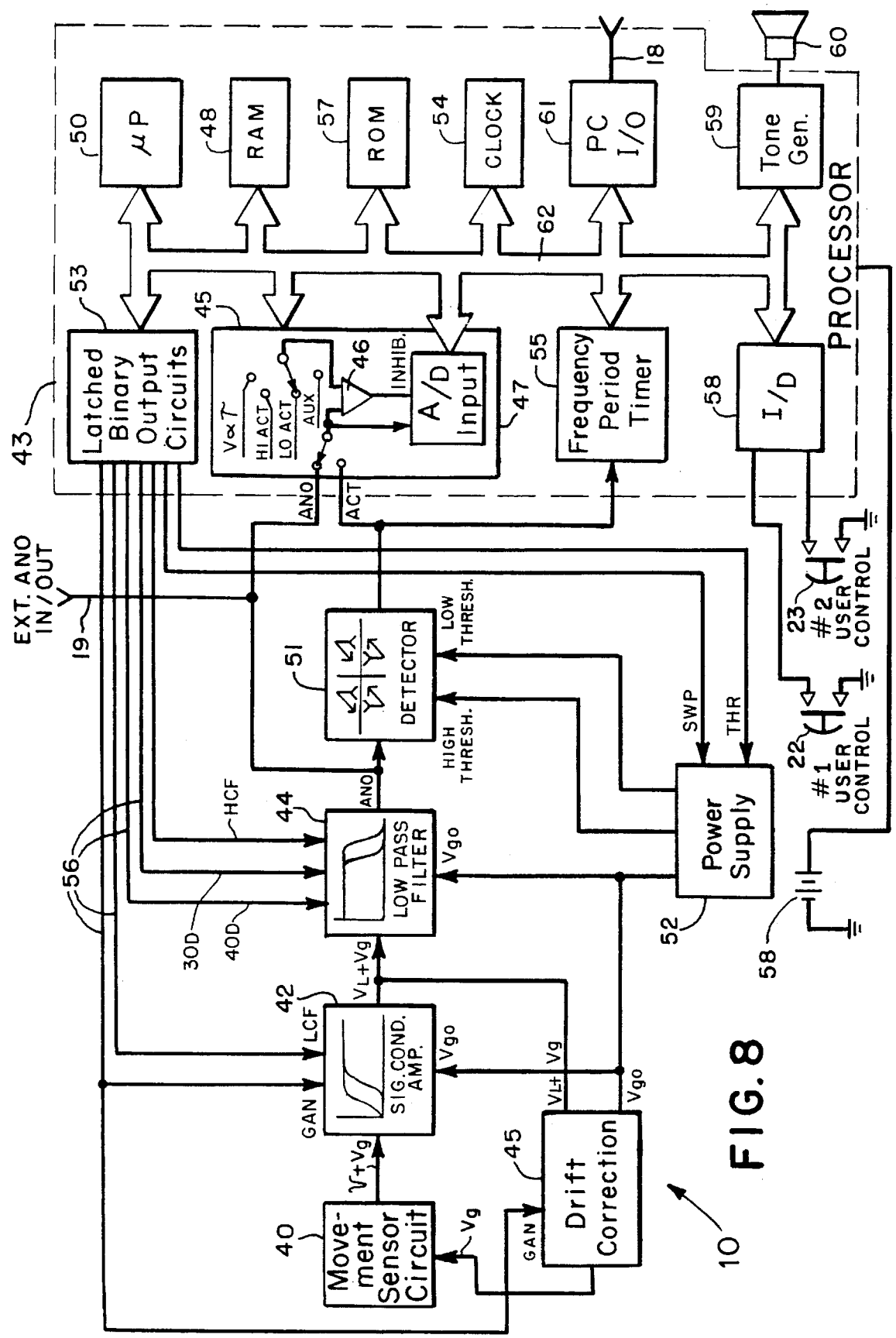
FIG. 8 is a functional block diagram showing the principal components and circuits of the activity monitor of FIGS. 1–3.

Referring to FIG. 8, within activity monitor 10 the bimorph beam assembly 30 is incorporated in a sensor circuit 40. Within this circuit the motion signal v developed by the bimorph beam is added to a voltage $V_g$ provided by a drift correction circuit 41.

Since the motion signal v generated by the beam contains harmonics at the beam resonant frequency, has relatively poor low frequency response and is of low amplitude, it is necessary that the motion signal be conditioned prior to analysis and storage. To this end, the resulting sensor output signal $v+V_g$ is applied to a conditioning circuit 42 comprising a configurable threshold high pass filter and configurable gain signal amplifier. Within conditioning circuit 42 the signal is AC and DC amplified, typically by AC factors of from 5–25 and a DC factor of 75–375, to provide a signal of sufficient amplitude that even visually imperceptible movements can be recognized and quantified without corruption due to DC drift. Undesired low frequency components resulting from other than body activity to be monitored, which are typically below 0.16 hertz, are attenuated. Since virtually all movement of a subject produces signals having frequencies that are above 0.16 hertz, valid data is not affected. Low level signals, such as result from heart beats or blood flow, are both above 0.16 hertz and are amplified for subsequent processing.

In accordance with one aspect of the invention, the low frequency threshold of the high pass filter amplifier 40 is configurable to either 0.16 hertz or 2 hertz to permit selective attenuation of low frequency signals associated with body activities such as breathing, which typically produce a signal between 0.2 and 1 hertz. Selection of the desired threshold is accomplished over a configuration control line LCF which receives an appropriate configuration signal from a processing and control circuit 43 contained within the activity monitor. Similarly, the gain of conditioning amplifier 42 is controlled by a configuration signal provided on a configuration control line GAN extending from processor circuit 43 to the amplifier. The effect of this configuration signal is to vary the AC gain of the conditioning amplifier from a high level, typically on the order of 25, to a low gain, typically in the order of 5. As will be seen presently, this is particularly useful in reconfiguring the activity monitor to analyze very low level motion signals, such as those associated with sleep.

The output of conditioning amplifier 42 ($v_f+v_g$) is applied to a low pass amplifier 44 and to a dc drift correction circuit 45. Within drift correction circuit 45 the amplifier output is compared with a fixed reference voltage $V_{g0}$, which comprises a virtual ground for the amplifier and filter circuitry, to generate the drift compensated signal $V_g$ for application to sensor circuit 40. In this way, the DC output level of conditioning amplifier 42 is continuously compared with a fixed reference voltage, and the voltage applied to the motion sensor is varied to prevent any deviation between the DC output level of the amplifier and the reference voltage. Consequently, any DC drift within the high gain conditioning amplifier circuit is eliminated. This makes it possible for the conditioning amplifier to operate at the high gains required for successful low level body activity detection and analysis.

The output of conditioning amplifier 42 is applied to a low pass filter 44 wherein high frequency components of the signal, such as produced by the natural resonance of the bimorph beam sensor, are attenuated. Low pass filter 44, in accordance with one aspect of the invention, can be configured by configuration signals applied on configuration control lines 30D, 40D and HCF by processor circuit 43 to obtain three different high frequency cutoff frequencies. In a preferred embodiment of the invention, filter 44 is configurable for thresholds of 1, 3 or 9 hertz.

Figure 10:
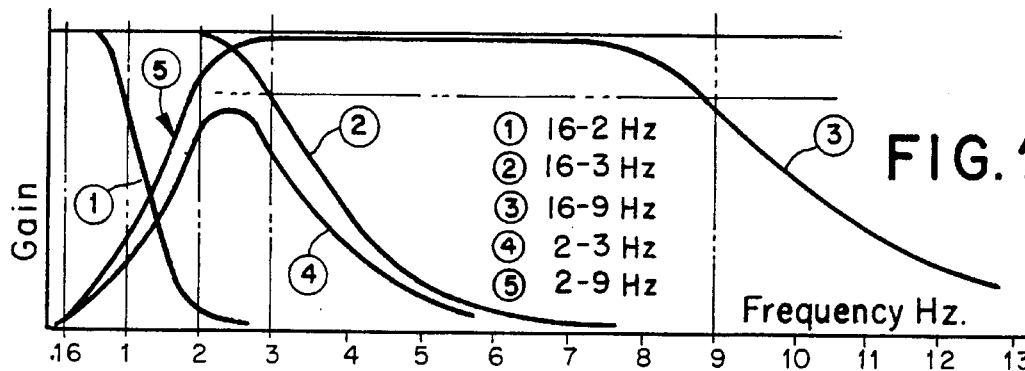
FIG. 10 is an illustrative plot of the frequency spectrum of five different activities of the human body.
Figure 11:
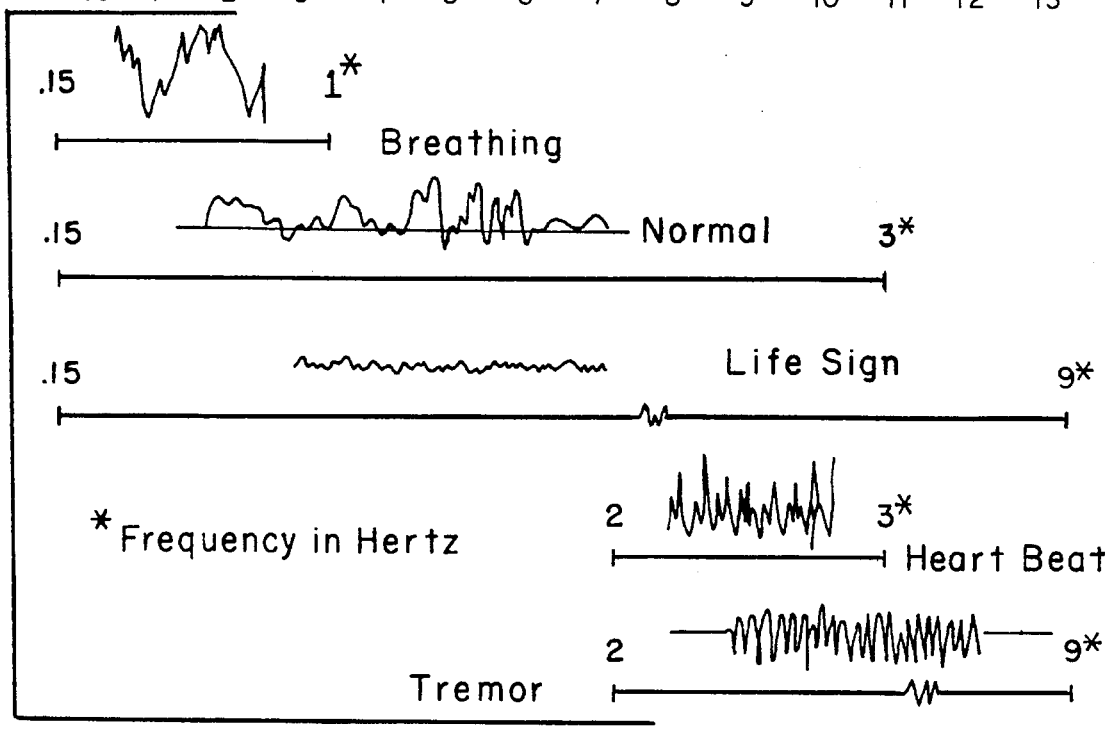
FIG. 11 is a simplified depiction of the frequency spectrum and signal characteristics of five specific activities of the human body.

Since the high pass filter of conditioning amplifier 42 can be configured with a threshold of either 0.2 or 2 hertz, and filter 44 can be configured with a threshold of either 1, 3 or 9 hertz, the monitor is advantageously able to collect information within a selected one of five distinct frequency ranges: 0.16 to 1 hertz; 0.16 to 3 hertz; 0.16 to 9 hertz; 2 to 3 hertz; and 2 to 9 hertz. This is illustrated in FIG. 10. As previously stated, and as illustrated in FIG. 11, the motion sensor when exposed to certain specific types of body movement produces signals which generally fall into these distinct ranges. Nighttime activity, such as sleep, produces a signal between 0.2 and 3 hertz. Breathing produces a signal between 0.2 and 1 hertz. Heart beats produce a signal between 2 and 3 hertz. Tremor activity produces a signal between 2 and 9 hertz. Accordingly, by configuring filters 42 and 44 to pass signals above a selected threshold and below another selected threshold, the activity monitor 10 can be configured in accordance with the invention to collect data only for certain specific types of activities of a subject.

The output of low pass filter 44, designated ANO, is applied to an analog-to-digital sampling converter 45 within processor 43. This circuit samples the analog ANO signal at a predetermined rate, for example, 10 samples per second, for application to an analog-to-digital (A/D) converter 47 within the sampling circuit. The signals are also applied to a comparator 46, wherein their voltage level is compared with one or more selected reference signals appropriate to the measurement being made. In particular, the reference signal may comprise either a low level reference for recognizing excessively low activity signals, such as might occur with negative saturation of the conditioning amplifier, a high level reference signal for recognizing excessively high activity signals, such as might occur with positive saturation of the conditioning amplifier, a reference signal proportional to repetition rate, as determined by the control unit, or an auxiliary signal provided by the monitor operating system for special measurement purposes. The output of comparator 46 inhibits operation of A/D converter 47 to prevent invalid data from being processed and stored, and signals the operating system of the invalidity. Valid data samples are converted by A/D converter 47 to digital signals with, for example, twenty levels of quantification, for storage and/or processing within processor circuit 43. Within processor 43 the digitized data signals may be transferred over a data bus 62 to conventional memory means, such as a RAM 48 for storage. With an exemplary sample rate of 10 byte samples per second, approximately 1 hour of data can be stored in a 32K byte memory.

Because direct digital recording of the data digitized by A/D converter 47 is generally memory intensive, the data is typically processed by a microprocessor 50 within processor 43 to obtain certain resultants from the data, which resultants are stored in RAM 48 in place of the data. The data processing, which typically takes place when the activity monitor is not collecting data, may include the computation of the average varience of the collected digital data for each epoch in which data was collected. Highest values and lowest values of the data for each of the epochs can also be calculated. After storage of the resultants, the data from which the resultants were obtained is erased from RAM 48. By retaining only the statistical resultants, the memory is unburdened and available to receive additional data for processing.

To determine whether information may have been lost during the processing, the processing may include a review of the high and low variance values. If these values exceed certain thresholds, the user is cautioned that that the number of epochs may be too large or too small.

The analog output signal ANO from low pass filter 44 is also applied to a window detector 51, which provides an output signal ACT when the input signal crosses predetermined maximum and minimum thresholds. The thresholds in the preferred embodiment include a high threshold voltage $V_H$ and a low threshold voltage $V_L$ which are symmetrically centered about the virtual ground reference voltage $V_{g0}$. Preferably, the absolute voltage difference between the two threshold voltages is greater than the amplitude of the noise ordinarily produced within the monitor so that only valid motion signals are recognized by the detector.

In accordance with another aspect of the invention, the upper and lower threshold can be reconfigured to accommodate specific processing requirements. In particular, the threshold voltages, which are supplied by a power supply circuit 52, can be selected to one of two discrete levels by a configuration signal conveyed from processor 43 to power supply 52 on a control line THR. The control signal is generated within processor 43 by latched binary output circuits 53. The output signal ACT is supplied through sampling circuit 45 to RAM 48, indicating that a crossing has occurred.

Microprocessor 50 in conjunction with a clock 54 calculates and records in RAM 48 the number of counts passed by detector 51 for the epoch in use, which may be specified by the user. For example, with the use of a ten second epoch, a five hertz motion signal will produce a total of one hundred counts. Threshold crossing data allows the frequency of the motion signal to be reconstructed.

Processor 43 preferably includes a timer circuit 55 which measures the amount of time the signal remains above or below the selected thresholds. The timing is begun when a count is received from detector 51 indicating that the signal has crossed the threshold and stops when a count is received indicating that the signal has crossed the threshold again. The total amount of time above or below the threshold for the given epoch may be recorded in memory 48.

The threshold crossing data and time across threshold data advantageously allows the analog waveform to be reconstructed. For example, by dividing the threshold crossing data by 2 one obtains the frequency of the signal. The amplitude of the signal produced by subject movement can be accurately estimated by further processing of threshold crossing data and time across threshold data according to the following equation:

$$Y = Y_0 \sec T/E$$

where Y is equal to signal amplitude, $Y_0$ is equal to threshold amplitude, T is equal to time above threshold and E is equal to epoch. The processing of the data to obtain the signal amplitude is performed by microprocessor 80 and stored in memory 48.

As stated above, the various components of activity monitor 10 are configurable to shape the signal produced by the sensor, to vary the sensitivity of the monitor, and to alter the data collected by and recorded in the memory 48. To this end, the monitor includes configuration control lines 56 by which the components can be configured. In one successful embodiment of the invention, the control lines 56 connect to solid state analog switch devices that can be switched by an applied logic-level control signal. Activity monitor 10 includes eight of such switch devices.

One of the configuration control lines, designated GAN, switches the amplification of the motion signal by conditioning amplifier 42 from a low state to a high state. A second configuration control line, designated HCF, switches filter 44 to cut off aspects of the signal above 9 hertz. Used in combination with the 30D control line and 40D control line, three high cutoff frequencies—at 1, 3 and 9 hertz—are realizable. A third configuration control line, designated LCF, switches conditioning amplifier-filter 42 to pass a signal having frequencies only above 2 hertz instead of above 0.16 hertz. A fourth configuration control line, designated THR, switches the high and low thresholds of window detector 51. A fifth configuration control line designated 30D, switches the decibel per octave rolloff of filter 44 to 30 for the 1 hertz cutoff. A sixth configuration control line, designated 40D, switches the decibel per octave rolloff of filter 40 to 40 for the 3 or 9 hertz cutoff. A seventh configuration control line, designated SWP, switches power on and off to the various circuits of monitor 10. The SWP control can be managed by clock 54 so that power is provided to the components only during predesignated time periods.

Processor 43, which may be conventional in construction and operation, includes the RAM 48 which has a storage capacity sufficient to, for example, store signal data, operating instructions, and other programs by which the monitor is operated. Preferably, control unit 43 also includes a ROM 57 wherein an operating system is stored by which the monitor is controlled. In accordance with one aspect of the invention, the RAM can accept programs which will control the monitor according to modes different from those modes stored in the ROM. In these instances, microprocessor 50 executes the instructions stored in the ROM and/or RAM by retrieving data and/or indications from the RAM or ROM, processing data, and returning data to the RAM of I/O ports in a manner well known to the art.

The processing and control circuit 43 includes a conventional input/output (I/O) circuit 58 for receiving inputs from user-actuated switches 22 and 23, and a tone generator 59 and transducer 60 for providing audio feedback to the user. A conventional PC I/O circuit 61 is provided to link the control circuits to the host computer through connector 18.

The various circuits contained within monitor control circuit 43 are linked by the bidirectional data bus 62. It will be appreciated that while the various control circuits are shown as separate circuits, one or more of the circuits may in fact be combined and contained within a single microchip, apart from or together with microprocessor 50. Furthermore, whether separate or combined, the circuits and microprocessor operate under control of software resident in RAM 48 or ROM 57 in a manner well known to the art.

Operating power for the monitor is obtained from a conventional coin cell 58, such as, for example, a 2.7 volt 150 ma-hr lithium cell. To prevent an insufficient voltage condition from occurring during periods of large power drain, such as when microprocessor 50 is writing into memory 48, which might cause spurious data to be stored, power supply 52 is preferably voltage regulated.

The activity monitor can be initialized to operate in one of three operating modes. In mode one, termed emulation mode, the monitor collects data only for the amount of time the motion signal is above a predetermined threshold. This pattern emulates a prior monitor. In mode two, termed "fixed initialization", once the monitor is initialized and disconnected from its computer, the monitor operates to collect certain types of data. In mode three, termed "floating initialization", a number of control operations are stored in RAM 48. The monitor initially operates according to a first set of instructions. At a predesignated point in time, for example, once every 24 hours, the monitor retrieves new instructions and the monitor circuits are reconfigured to operate to collect data according to a new set of instructions. Data obtained according to each set of instructions is stored sequentially. To identify the transition from one set of instructions to another, a marker is entered on a time line in the data channel of the monitor.

In the fixed initialization mode, the user designates the configuration of the monitor circuitry to be used in collecting data. To facilitate this selection, the various possible configuration variables are grouped and assigned individual numbers. An advantageous set of configuration variable groupings is provided in Table 1 below.

TABLE 1

| | Configuration Groupings | | |
|---|---|---|---|
| Grouping | Bandpass | High/Low Gain | High/Low Sensitivity |
| 1 | .1–1 hz | High Gain | High Sensitivity |
| 2 | .1–1 hz | High Gain | Low Sensitivity |
| 3 | .1–1 hz | Low Gain | High Sensitivity |
| 4 | .1–1 hz | Low Gain | Low Sensitivity |
| 5 | .1–3 hz | High Gain | High Sensitivity |
| 6 | .1–3 hz | High Gain | Low Sensitivity |
| 7 | .1–3 hz | Low Gain | High Sensitivity |
| 8 | .1–3 hz | Low Gain | Low Sensitivity |
| 9 | .1–9 hz | High Gain | High Sensitivity |
| 10 | .1–9 hz | High Gain | Low Sensitivity |
| 11 | .1–9 hz | Low Gain | High Sensitivity |
| 12 | .1–9 hz | Low Gain | Low Sensitivity |
| 13 | 2–3 hz | Low Gain | High Sensitivity |
| 14 | 2–3 hz | Low Gain | Low Sensitivity |
| 15 | 2–9 hz | Low Gain | High Sensitivity |
| 16 | 2–9 hz | Low Gain | Low Sensitivity |
| 17 | 2–3 hz | High Gain | High Sensitivity |
| 18 | 2–3 hz | High Gain | Low Sensitivity |
| 19 | 2–9 hz | High Gain | High Sensitivity |
| 20 | 2–9 hz | High Gain | Low Sensitivity |

In the fixed initialization mode, the user may assign definitions, or "event variables" to user input switches 22 and 23. For example, operation of the switches may cause one or more markers to appear in the data recorded in RAM 48 depending on the meaning assigned to them.

In the fixed initialization mode, the user may also choose the type of data which is to be recorded. These variables are termed "data variables". The types of data that may be selectively recorded are outlined in Table 2 below:

TABLE 2

| | Data Recorded |
|---|---|
| Designation | Type of Data |
| ZCA | Crossing above threshold (in counts) |
| ZCB | Crossing below threshold (in counts) |
| ZAB | Crossing above and below threshold (in counts) |
| TCA | Time above threshold (in time) |
| TCB | Time below threshold (in time) |
| TAB | Time above and below threshold (in time) |
| AAD | Recording of waveform directly by digital conversion |

In the floating initialization mode, the user can choose, for example, to configure the monitor to provide and record information according to one set of instructions, and then at a designated point in time established by clock 54 provide and record information according to another set of instructions, without having to reconnect the monitor, via the interface unit, to the host computer. The floating initialization mode provides two options to the user: "fixed floating" and "floating floating".

In the "fixed floating" option mode, the user can establish a schedule by which configuration variables, event variables, and data variables are changed. With this option, changes to the variables may be scheduled often, but to provide the collection of meaningful comparable data, preferably no more often than once every other epoch.

In the "floating floating" option mode, the variables are changed according to the nature of the data that has been collected, rather than according to a strict schedule. Accordingly, for example, if a certain choice of configuration variables leads to the saturation of the memory, the variable can be changed automatically to avoid saturation. The instructions by which these variables will be changed are contained in a program stored in RAM 48.

Figure 9:
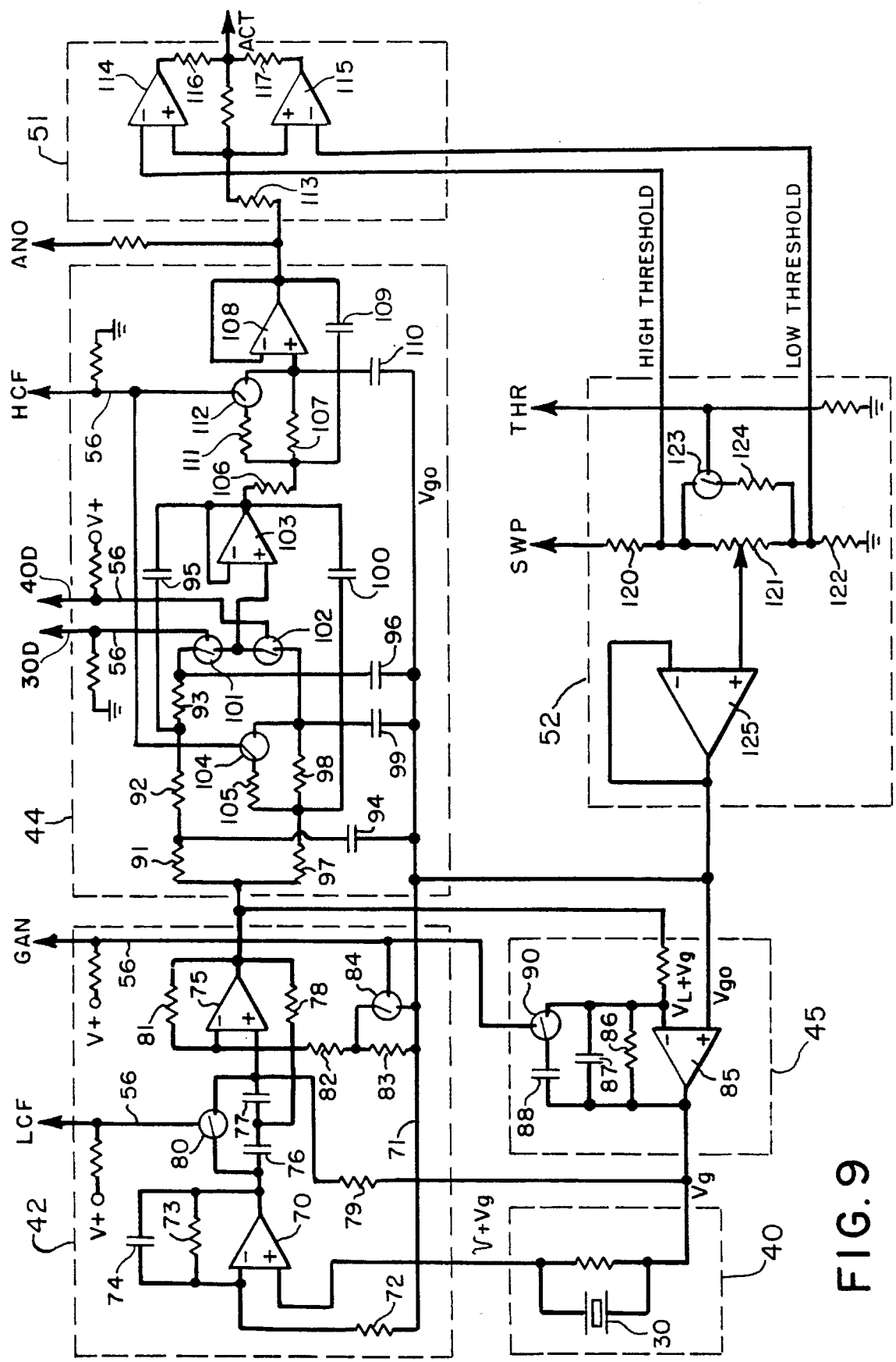
FIG. 9 is a simplified schematic diagram of the activity monitor described in FIG. 8.
Figure 12:
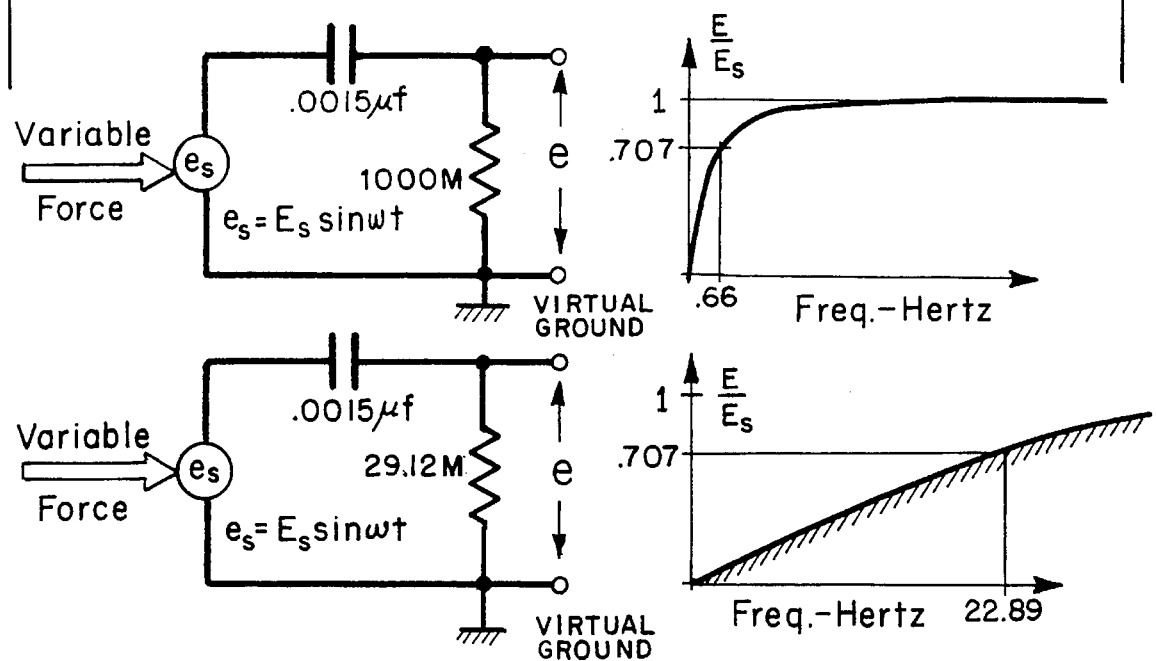
FIG. 12 is a simplified schematic diagram and plot illustrating the characteristics of the piezoelectric bimorph beam sensor utilized in the activity monitor of the invention.

Referring to the simplified schematic diagram shown in FIG. 9, the various stages of monitor 10 are shown implemented using conventional electronic components and techniques. As illustrated in FIG. 12, the bimorph beam motion sensor is a true bipolar device which produces an oscillatory voltage (typically ±1 volt for full deflection) in response to an oscillatory force and does not respond to a continuous force. The bimorph series capacitor greatly attenuates the low frequency output of the sensor.

The attenuating voltage produced by the piezoelectric bimorph beam transducer 30 plus the offset voltage $V_g$ is applied to the non-inverting input of a first differential amplifier 70 within conditioning amplifier 42. The inverting input is connected to a virtual ground bus 71 by a resistor 72, and resistor 73 and capacitor 74 connected between the output of the differential amplifier and the inverting input provide feedback to stabilize the amplifier.

The output of differential amplifier 70 is applied to a second differential amplifier 75 through a highpass filter network comprising capacitors 76 and 77 and a resistor 78 and 79. An analog switch device 80 connected in parallel with capacitors 76 and 77 enables these devices to be selectively reconfigured relative to the input of amplifier 75. When switch device 80 is closed, the capacitors and associated components provide a lower cutoff frequency to the applied signal, typically in the order of 0.16 hertz, and when the switch is open, provide a higher cutoff of approximately 2 hertz.

The operation of analog switch device 80 is controlled by a logic signal applied on configuration control line LCF, which comprises one of the control lines 56 selectively utilized by processor circuits 43.

The inverting input of the second differential amplifier 75 includes a feedback network comprising resistors 81, 82 and 83, which control the gain of the amplifier. An analog switch device 84 connected across resistor 83 allows this network, and hence the gain of amplifier 75, to be changed. Switch device 84 is actuated by a signal on the GAN configuration control line provided by processing circuit 43.

Figure 14:
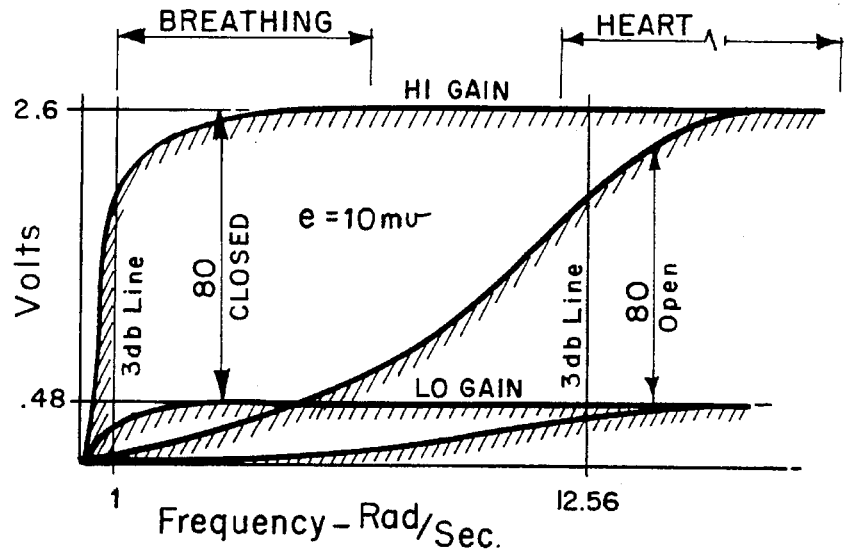
FIG. 14 is a graphical depiction of certain bandpass characteristics associated with the high-pass filter utilized in the activity monitor shown in FIGS. 8 and 9.

Resistor 78 and capacitors 76 and 77 together with differential amplifier 75 form a highpass filter having a threshold dependent on the status of analog switch device 80. In practice, switch device 80 is selectively rendered conductive or non-conductive by configuration control signals on the LCF configuration control line by processor circuit 43 to achieve a desired frequency and gain characteristic in the motion signal conditioning circuit. The result of the two gain configurations, coupled with the two cutoff frequency configurations, is shown in FIG. 14.

In practice, it has been found that selecting the filter components to contain three negative highly damped roots providing a Butterworth response, with a relative sharp rise to the 3 db point, provides a maximally flat passband and minimum signal distortion.

The output of amplifier 75, which may contain a DC drift component resulting from input offset and bias current errors in that amplifier and in amplifier 70 (which together may have a gain as high as 400), is applied to a drift correction amplifier 45. There, the voltage is compared with an absolute reference voltage $V_{go}$ applied to the other non-inverting input of the amplifier. The resulting signal $V_g$ is applied to the bimorphous beam transducer 30 in motion sensing circuit 40. A feedback circuit comprising a resistor 86 and a pair of capacitors 87 and 88 is provided between the output of amplifier 85 and the inverting input to introduce a time constant to prevent the motion signal from also being nulled. So that the response of the amplifier will be slower when amplifier 75 is operating at higher gain levels an analog switch device 90 is provided in series with capacitor 88. This switch device is controlled by the GAN configuration control line such that the capacitor is switched into the circuit under higher gain conditions for amplifier 75.

The two amplifiers associated with low pass filter 44 are not included in the hulling loop since these are operated in a voltage follower mode and would therefore contribute only their input offset voltage error to the amplifier motion signal.

Figure 13:
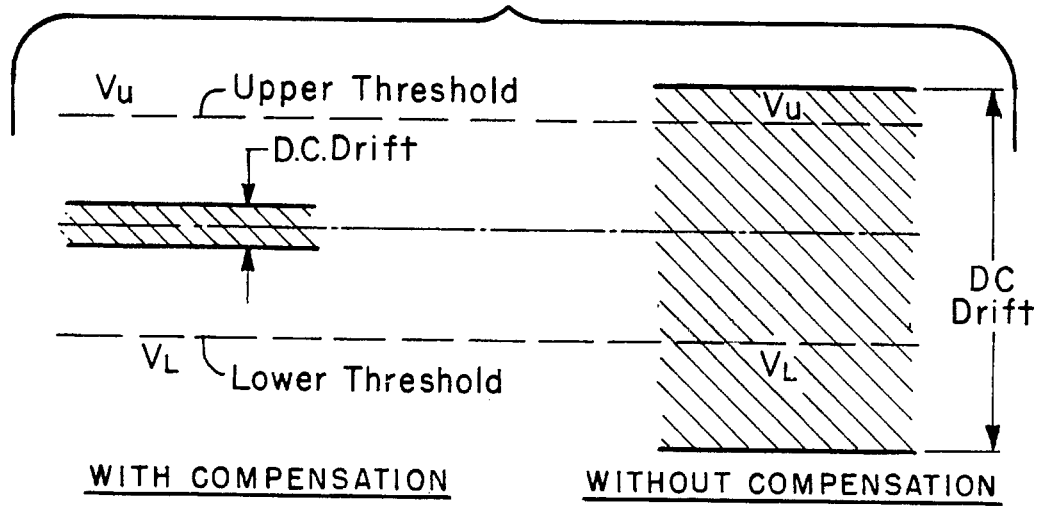
FIG. 13 is a graphical depiction of certain voltage relationships associated with the window detector utilized in the activity monitor of the invention.

As shown in FIG. 13, the overall dc error must be kept small for proper operation of window detector 51. Any appreciable dc drift results in a zero crossing of one of the thresholds or a loss of detection symmetry.

The conditioned output signal developed by conditioning circuit 42 is applied to a first lowpass filter network comprising resistors 91, 92 and 93 and capacitors 94, 95, and 96, and to a second highpass filter network comprising resistors 97 and 98 and capacitors 99 and 100. The two networks are connected by respective ones of two analog switch devices 101 and 102 to the non-inverting input of a first differential amplifier 103 within highpass filter circuit 44.

with this arrangement, depending on the status of analog switch devices 101 and 102, either the first or second filter network is coupled to the non-inverting input of differential amplifier 103. The selection is made by configuration signals applied to the switch devices on configuration control lines 30D and 40D under the direction of processing circuit 43. A further adjustment to the second filter network is provided by an analog switch device 104 which connects a fixed resistor 105 in parallel with resistor 98 to change the operating characteristic of the network. Analog switch device 104 is controlled by configuration control line HCF under the direction of logic-level. configuration signals generated in the processing circuit 43.

The output of differential amplifier 103 is connected through a pair of serially-connected resistors 106 and 107 to the non-inverting input of a second differential amplifier 108 in lowpass filter circuit 44. Resistors 106 and 107 form, together with a capacitor 109 and 110 connected between the juncture of the two resistors and the output of amplifier 108, an additional lowpass filter network. Amplifiers 103 and 108 operate at unity gain, their outputs being connected directly to their inverting inputs. The cutoff frequency of the third network formed by resistors 106 and 107 and capacitor 109 and 110 can be selectively changed by means of a resistor 111 and an analog switch device 112 connected across resistor 107. Switch devices 112 and 104 operate together in response to logic-level configuration signals on configuration control line HCF to vary the cutoff frequency of lowpass filter circuit 44. The two filter networks of low pass filter 44 are each four pole Butterworth networks.

The output of lowpass filter circuit 44 is connected through a resistor 113 to a window detector comprising differential amplifiers 114 and 115. This signal is applied concurrently to the non-inverting inputs of these devices, and a high threshold reference voltage is applied to the inverting input of amplifier 114, and a low threshold reference signal is applied to the inverting input of amplifier 115. The outputs of the amplifiers are connected together by resistors 116 and 117 such that an output is produced upon each zero crossing of the thresholds established by the two reference voltages.

The reference voltages are obtained in a power supply circuit 52 by means of a voltage divider comprising resistors 120, 121 and 122 connected between line SWP, which comprises a switched power source within the processor and control circuit 43, and case ground. An analog switch device 123 and capacitor 124 selectively change the center resistance in the voltage divider such that the voltage level of the high threshold is reduced and the voltage level of the low threshold is increased. This results in a smaller window for the detector and is under control of logic-level configuration signals applied to the THR configuration control line by the processor and control circuit 43.

The voltage divider comprising resistors 120–122 also provides the reference voltage $V_{go}$ through a voltage follower amplifier 125. The reference voltage $V_{go}$ thus developed is also utilized as a virtual ground in filter circuits 42 and 44. Potentiometer 121 permits fine adjustment of the virtual ground voltage $V_{go}$ to obtain a zero offset error at detector 51.

As previously discussed, as a result of the six control lines GAN, LCF, 30D, 40D, HCF and THR the activity monitor can be configured to collect and analyze data specific to selected conditions. To this end, the latch binary output circuits 53 produce binary logic-level configuration signals (which may be designated logic 1 or logic 0) on configuration control lines 56 for application to the various analog switches contained in the circuitry of the actigraph. For the twenty possible test conditions (option numbers 1–20) configuration signals are generated as indicated below in Table 3:

TABLE 3

| OPTION NUMBER | HCF | SWP | HRN | LCF | THR | GAN | 30D | 40D | BANDPASS |
|---|---|---|---|---|---|---|---|---|---|
| 1 | 1 | 1 | 1 | 1 | 1 | 1 | 1 | 0 | 0.1–1 hz HG LT |
| 2 | 1 | 1 | 1 | 1 | 0 | 1 | 1 | 0 | 0.1–1 hz HG HT |
| 3 | 1 | 1 | 1 | 1 | 1 | 0 | 1 | 0 | 0.1–1 hz LG LT |
| 4 | 1 | 1 | 1 | 1 | 0 | 0 | 1 | 0 | 0.1–1 hz LG HT |
| 5 | 0 | 1 | 1 | 1 | 1 | 1 | 0 | 1 | 0.1–3 hz HG LT |
| 6 | 0 | 1 | 1 | 1 | 0 | 1 | 0 | 1 | 0.1–3 Hz HG HT |
| 7 | 0 | 1 | 1 | 1 | 1 | 0 | 0 | 1 | 0.1–3 hz LG LT |
| 8 | 0 | 1 | 1 | 1 | 0 | 0 | 0 | 1 | 0.1–3 hz LG HT |
| 9 | 1 | 1 | 1 | 1 | 1 | 1 | 0 | 1 | 0.1–9 hz HG LT |
| 10 | 1 | 1 | 1 | 1 | 0 | 1 | 0 | 1 | 0.1–9 hz HG HT |
| 11 | 1 | 1 | 1 | 1 | 1 | 0 | 0 | 1 | 0.1–9 hz LG LT |
| 12 | 1 | 1 | 1 | 1 | 0 | 0 | 0 | 1 | 0.1–9 hz LG HT |
| 13 | 0 | 1 | 1 | 0 | 1 | 0 | 0 | 1 | 2–3 hz LG LT |
| 14 | 0 | 1 | 1 | 0 | 0 | 0 | 0 | 1 | 2–3 hz LG HT |
| 15 | 1 | 1 | 1 | 0 | 1 | 0 | 0 | 1 | 2–9 hz LG LT |
| 16 | 1 | 1 | 1 | 0 | 0 | 0 | 0 | 1 | 2–9 hz LG HT |
| 17 | 0 | 1 | 1 | 0 | 1 | 1 | 0 | 1 | 2–3 hz HG LT |
| 18 | 0 | 1 | 1 | 0 | 0 | 1 | 0 | 1 | 2–3 hz HG HT |
| 19 | 1 | 1 | 1 | 0 | 1 | 1 | 0 | 1 | 2–9 hz HG LT |
| 20 | 1 | 1 | 1 | 0 | 0 | 1 | 0 | 1 | 2–9 hz HG HT |

In operation, the activity monitor of the invention, by reason of its ability to analyze selected types of data in response to internally and externally provided programming instructions is extremely useful in analyzing human activity. Although human motion is complex, it has been determined that movement of the non-dominant wrist tends to correlate with body activity, muscle movement and brain activity. Thus, properly analyzed, wrist motion can be used to infer many useful facts about human activity.

It has been determined that virtually all human motion can be captured in a frequency band from approximately 0.15 hertz to 8 hertz. Furthermore, it has been determined that uniaxial sensing is adequate for sensing human motion because human motion is not polarized. It is possible to find different power spectrums for humans suffering from disorders that manifest themselves as behavior modification. For example, individuals having neurological disorders, such as Parkinson's disease, can produce an inversion of the normal spectrum producing peaks beyond 3 hertz. From an analysis of many data collections it has been determined that certain normal and abnormal human activity can be found within certain defined frequency bands, as shown in FIG. 11.

The dynamic range of human motion is large, typically in the order of 1000 to 1. For this reason it is critical that the gain of any amplifier used to sense analog motion be appropriately scaled. In the activity monitor of the present invention, the scaling is accomplished automatically by the monitor processor circuit 43. This ability is particularly useful where human activity is observed both during the day, when activity is greater, and at night, when activity usually decreases dramatically during sleep. The ability to schedule changes in gain according to the time of day allows the activity monitor of the present invention to optimize signal resolution and avoid signal saturation. This is also true of the ability to switch frequency bands.

No single unit of measurement exists for body activity. Early activity monitors used Mercury switches to detect motion. These were position sensors as well as motion sensors. The data from these early devices was related to frequency of motion but not to amplitude. The early devices were based on the theory that activity could be equated to the frequency of occurrence. The more often the subject moved, the greater his activity.

A later activity monitor, such as the Model AM-16 manufactured by Precision Control Design, Inc. utilized linear sensing and analog filtering to shape the input activity signal and filter out artifacts. This device utilized a piezoelectric bimorph beam fitted with an offset proof mass. The use of a lowpass filter eliminated the natural resonant frequency of the bimorphous beam and allowed only signal frequencies within the body's capability to be passed on to the detector.

The Model AM-16 offered analysis of the motion signal utilizing a zero crossing detector to provide counts of threshold crossing.

The zero crossing detector is a threshold detector. When the activity signal exceeds a predetermined threshold a count is produced. A microprocessor counts each transition that occurs within an epoch, or measurement period. For example, a 5 hertz signal at an amplitude of 15 millivolts produces 10 crossings so that if the epoch is 10 seconds the total counts per epoch is 10. The process is repeated until the entire memory is filled with counts per epoch data chronologically organized. Zero crossing detection ignores amplitude.

Figure 15:
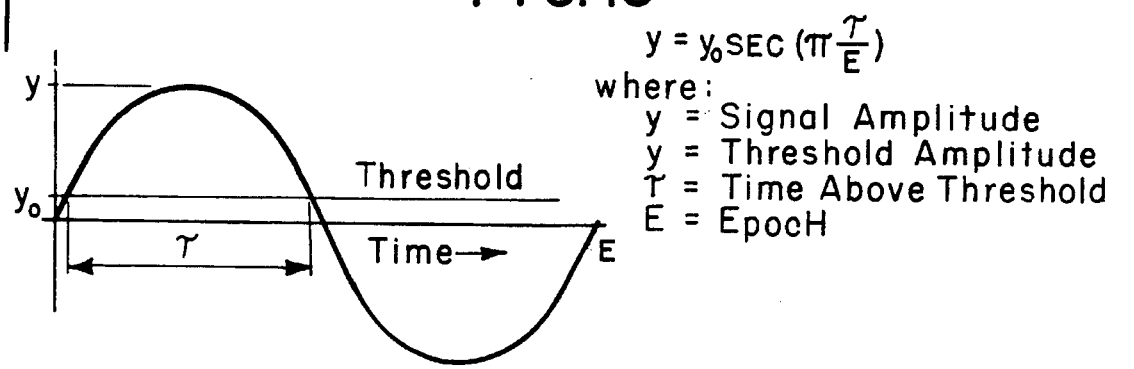
FIG. 15 is a depiction of a sinusoidal waveform illustrating certain parameters thereof.

Time above threshold is closely related to signal amplitude. Zero crossing and time above threshold are both threshold techniques but produce independent data sets. Either can be derived from the other. For a sinusoidal waveform the amplitude of the waveform can be uniquely derived by knowing how long the wave stays above a threshold line. This is illustrated in FIG. 15.

Figure 16:
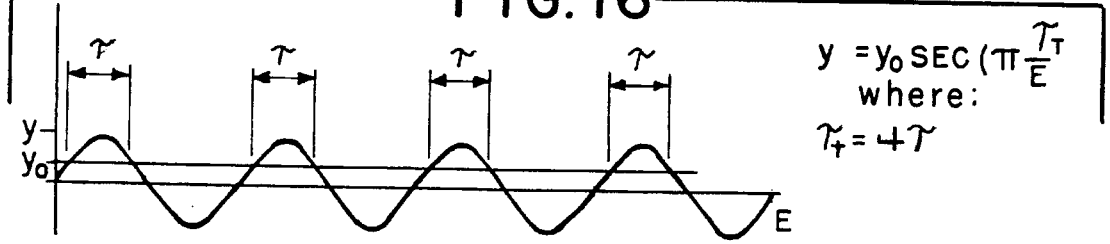
FIG. 16 is a depiction of a repetitive waveform showing certain zero-crossing parameters thereof.

Since actigraphy deals with many transitions in a given epoch the relationship between amplitude and time can be expanded to include more than one cycle as shown in FIG. 16 where, it is seen that short epochs can produce a harmonic-like waveform containing data that is approximately sinusoidal. Summing time above threshold for a given epoch is the only data needed to estimate the amplitude of the actual waveform.

Both time above threshold and signal amplitude are recorded by the activity monitor of the present invention. The two threshold modes when taken simultaneously provide both amplitude and frequency information about the signal. Zero crossing activity measured in counts per second divided by two is the frequency. Time above threshold activity data yields amplitude information. The two taken together allow a good reconstruction of the analog waveform from which each was derived. It is important to remember that this reconstruction can be accomplished from recorded data utilizing far less memory than if traditional analog-digital conversion were employed.

The activity monitor of the present invention incorporates an analog-to-digital converter that enables the waveform to be recorded directly. This is memory intensive, requiring about 10 bytes of memory per second. For an available memory of 32K only 53 minutes of data collection is possible. Since most applications for an activity monitor run for days or even weeks, this is not acceptable in many applications. Absent substantially larger memories and battery capacity, direct analog-to-digital conversion and storage is practical only for very limited applications.

Since human motion is highly variable throughout the day and from day to day, no single set of data collection parameters is sufficient to adequately cover the full range of human activity experienced by an activity monitor. To be useful in clinical applications, the activity monitor must be adaptable to dramatic changes in human activity over a typical 24 hour recording period. To enable the activity monitor of the invention to operate under these widely varying conditions, an operating system AOS is incorporated into activity monitor 10 as a base line program to enable the monitor to incorporate many different hardware and software configurations.

The activity monitor of the invention can operate internally, externally or in a combination mode. In the internal mode the AOS program code operates the unit. In the external mode a program loaded into RAM 48 operates the unit. In a combination mode the activity monitor operates from both ROM and RAM. The microprocessor 50 of the activity monitor is directed by specific software algorithms, which may be provided by users to customize the operation of the unit for a specific purpose. Once installed, an external program can alter hardware, control initialization, determine data collection modes and invoke new operating rules based upon real time analysis of data being collected. A single activity monitor with appropriate RAM-loaded algorithms can be used to study hyperactivity, tremors, sleep deficiencies, shift work, ergonomics, dementia, rheumetism, drug side effects, athletic exertion, jet lag, and virtually any form of human mobility.

When human activity follows a predictable routine during a typical 24 hour monitoring period, apriori programming of the activity monitor can be employed to optimally configure the machine according to a scheduled protocol. However, in cases where abnormal sleep and neurological disorders follow no routine or predictable pattern, it is highly desirable that the activity monitor learn contemporaneously with data collection. The activity monitor of the present invention has this capability.

Figure 17:
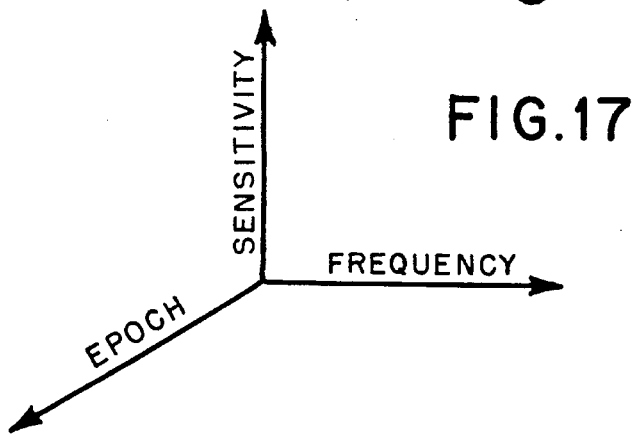
FIG. 17 is a three-dimensional depiction of certain axes useful in analyzing activity of the human body.
Figure 18:
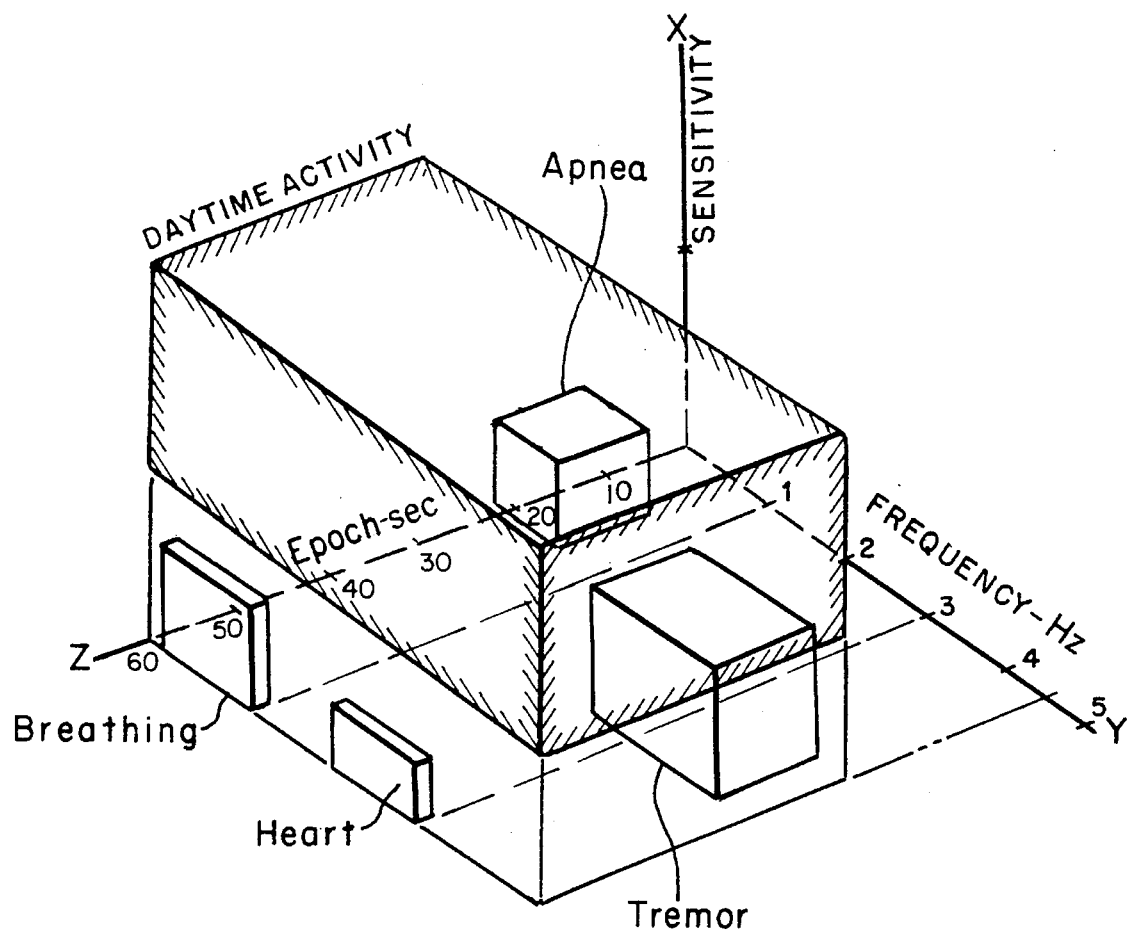
FIG. 18 is a 3-dimensional depiction of certain activities of the human body viewed along the axes of FIG. 14.

Three mutually orthogonal parameters may be used to define regions in space which have clinical importance, as shown in FIG. 17. Frequency, sensitivity and epoch have precise meanings:

Frequency—refers to either the activity monitor bandwidth or the spectral content of the input activity signal. It is related to zero crossing.

Sensitivity—is a measure of the activity monitor's ability to detect motion. It is a function of voltage gain, comparator threshold and comparator hysteresis.

Epoch—is a time interval over which data is collected and may be thought of as an averaging window.

As previously developed, the ability to partition the human motion spectrum into frequency bands is important. Nighttime activity can be observed with good fidelity between 0.2 and 3 hertz, but tremor activity requires a bandwidth of 2 to 9 hertz. Breathing can be found between 0.2 and 1 hertz and heart beat between 2 and 3 hertz. It is possible, therefore, to partition the frequency axis into regions where specific types of motion can be observed independently of coexisting motion.

However, frequency itself is not a sufficient criteria for separating and observing important activity. It is desirable to utilize sensitivity to further discriminate and isolate motion of interest. For example, if a particular study involves determining the total number of minutes of sleep, it is not desirable to record heart rate or breathing which can be detected over the standard sleep band of 0.2 to 3 hertz. By reducing amplifier gain and increasing the detection threshold, these two signals drop out, but bulk body and wrist motions do not. This is because the bulk motions create large amplitude signals easily detected by the detector circuitry. Similarly, daytime activity resides in the 0.2 to 3 hertz band but nighttime sensitivity is too high and will cause amplifier saturation and loss of higher energy daytime activity. Reduction of sensitivity overcomes this problem.

Epoch is a time interval over which data is collected. Small epochs of 10 seconds provide a high resolution plot with much detail. Large epochs lose information and are not generally suitable for study of human activity. For example, if an epoch were set at 8 hours for a nighttime study all that would be learned is the total counts during sleep and a course average of counts per unit time. Nothing would be learned about total minutes of sleep nor sleep quality— important findings in sleep research. Nighttime epochs of 1 minute however provide good resolution and enable detection of sleep periods and non-sleep periods. Therefore, epoch may be thought of as an averaging window. If the window is too wide, information will be lost as in any averaging scheme. If the window is too narrow, it may be difficult to detect long period activity although it is always possible to create wider epochs if smaller epochs are used during data collection, the limiting factors being memory, size and test duration.

The activity monitor 10 of the present invention provides seven primary data output channels.

Channel 1. Zero crossing—Any time the analog motion signal exceeds or falls below the limits of a window comparator, a count is recorded. This output has four subsets:
 a. A single channel and only signal crossings above threshold.
 b. A single channel and only signal crossings below threshold.
 c. Dual channels of data, one for crossings above threshold and one for crossings below threshold.
 d. Crossings above and below threshold recorded as a single channel.

Channel 2. Time above threshold—Any time the analog motion signal exceeds or falls below the limits of a window comparator, the time it takes for the signal to arrive back within the window is recorded. There are four subsets identical to the zero crossing case above, namely, three types of single channel data and one dual channel data set. Time above threshold data is logged similarly to zero crossing except that total time per epoch is recorded instead of counts per epoch. It is also possible to record mixed data.

In this mode two channel data is recorded as previously described but one channel is zero crossing while the other is time above threshold. Amplitude data can also be recorded by using the secant and transformation.

Channel 3. The analog signal is sampled, digitized and recorded. With a 32K byte RAM the instrument provides one hour of one byte data at a maximum cutoff of 5 hertz.

Channel 4. May provide AND or ACT to external devices or may accept external digital controls.

Channel 5. A saturation channel when data is collected in zero crossing or time above threshold modes. The raw analog output is compared with a saturation reference voltage. Any time the analog voltage exceeds or falls below this limit, the instrument disregards all data in the current epoch and inserts a dummy count recognizable by an external reader program. The saturation channel and activity data are presented as overlapping data.

Channel 6. Provided this option is selected, pressing the event button places a time marker in the event channel. The event channel, saturation channel and activity data are presented as overlapping data.

As previously described, activity monitor 10 can be initialized to run in one of three modes selected by the user:

Option 1—Emulation—In this mode the activity monitor collects only 16K of single channel data above a threshold.

Option 2—Fixed Initialization—In this mode once the activity monitor is removed from the interface unit no changes to the operating parameters can occur, except for an AGC option wherein monitor gain is reduced or increased depending on the status of the saturation channel.

Option 3—Floating Initialization—An initialization protocol based on a 24 hour clock is programmed. At various times during the 24 hour period an interrupt occurs that momentarily shuts down data collection and causes the monitor to retrieve new initialization data and automatically restart. Data is stored sequentially. During the period of data collection cessation of one of the two event mark event channels will automatically place a marker on the event channel time line. This option also enables the monitor to use heuristically derived RAM loaded operational code.

Initialization in the fixed initialization mode incorporates the basic parameters needed to operate the monitor plus much more. Of most importance are the configuration variables which define a specific configuration for the monitor. There are seven processor configuration control lines which switch between logic low and logic high. Six of these lines set up the monitor with proper bandwidth, sensitivity and gain. When start time is reached, the seventh control line, SWP, switches from low to high, thereby powering the analog circuitry of the monitor (the digital circuitry of the processor circuit is continuously powered). The six configuration control lines then switch from minimum current drain (quiescence state) to the configuration specified at initialization. The seven configuration lines are defined as follows:

SWP Switches power to analog circuitry

GAN Amplifier gain either high or low

HCF High corner cutoff filter switches from 3 hertz to 9 hertz

LCF Low corner turn on filter switches from 0.16 hertz to 2 hertz

THR Detection threshold above virtual ground either high or low 30D 30 decibels per octave rolloff, 1 hertz cutoff only 40D 40 decibels per octave for 3 or 9 hertz cutoff Users never control these variables directly. Instead, they select a configuration from a table of options. The options and the associated configuration variables are shown in Table 3 above.

An event variable can be initiated by the two membrane switches 22 and 23. Actuating switch 22 causes the monitor to respond with two audible beeps and to log an event in channel 6. Actuating switch 23 causes the monitor to respond with one beep followed by a 5 second period of beeps synchronized with 1 second clock pulses followed by 10 seconds of activity pulses. Event variables are distinguished from configuration variables because their meaning can change according to a specific user requirement. For example, special sub-routines can be executed from RAM.

Data variables control the type of activity data that will be recorded. They are distinguished from configuration variables because they configure software and not hardware. It was previously noted that the monitor produces analog and digital outputs. These are provided simultaneously through the inner connect pins ANO and ACT. As previously described, seven types of data can be recorded from these two outputs:

ZCA—Zero crossing above threshold in counts

ZCB—Zero crossing below threshold in counts

ZAB—Zero crossing above and below threshold in counts

TCA—Time crossing above threshold in time

TCB—Time crossing below threshold in time

TAB—Time crossing above and below threshold in time

AAD—Analog out a/d conversion

At the time of initialization, the user typically selects one of the seven options listed. The activity monitor 10 then collects data for the full duration of its run-time. This is in the fixed initialization mode.

With the floating initialization, many of the initialization variables can be changed according to a predetermined schedule and the nature of the data being collected. This amounts to apriori and adaptive hardware and software reconfiguration during run-time. In the case of data variables, the monitor can change from one type to another according to a schedule or because of some data characteristic. For example, a simple experiment might use a protocol that requires alternating between ZCA and TCA. A more advanced experiment could require simultaneous recording of ZCA and TCA. The monitor may periodically examine a limited past data record for the purpose of evaluating whether or not the correct data mode (actually any variable under control of the processor) is in effect. Recognizing the limited amount of AAD data that may be gathered during a single run-time leads to possible special cases where only limited periods of analog activity are to be recorded by the analog channel. They are determined on the basis of historical data contemporaneously recorded and evaluated. This concept embraces a type of artificial intelligence that may optimize the monitor for recording wide dynamic range variable bandwidth data from human motion.

In one type of auto mode, the activity monitor gain is automatically switched according to the following algorithm:

If V analog is greater or equal than V SAT for 60% of epoch, then choose lower gain for not less than 10 minutes or less than 100 epochs. If V analog is less than or equal to 0.2 volts for 60% of epoch, then choose high gain for not less than 10 minutes or less than 100 epochs.

Floating initialization permits the activity monitor to alter its initialization and other parameters while in operation. Users may now input a schedule consisting of sets of initialization parameters or an algorithm. At various times the monitor will interrupt data collection and retrieve new initialization parameters just as if it had been inserted into the monitor and re-initialized. In the fixed floating mode the user provides a schedule of re-initialization parameters. The format for these parameters are the same as that used in the fixed initialization case.

In the floating floating initialization, initialization parameters are controlled by the nature of the data being collected instead of by apriori schedule. This is an adaptive situation. For example, a particular test might result in no analog saturation but saturation in zero crossing. This is a frequency problem and can be remedied one way by filter switching. In practice, the method is selected at the time of initialization by the user. A user-written program installed in RAM will initialize the monitor for the start time. One of the event channels is used to monitor the initialization parameter changes, and this information becomes a part of the data record. Floating floating and fixed floating initialization methods can be combined. Some parameters are not subject to adaptive change but are under control of a master schedule. Others are modified according to a user-specified algorithm that utilizes activity data to decide the best hardware and software configuration to choose contemporaneously with an on-going test.

While a particular embodiment of the invention has been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

I claim:

1. A method of automatically monitoring predetermined body movements of a patient subject over time by isolating said predetermined body movements from general body movements, said method comprising:

providing an activity monitor capable of producing an analog electrical signal responsive to body movements of said patient subject, said activity monitor being capable of detecting said predetermined body movements by isolating said predetermined body movements from general body movements by adjusting characteristics of said analog electrical signal to enhance relevant signal information indicative of said predetermined body movements while removing irrelevant signal information indicative of general body movements;

defining within said activity monitor a mutually orthogonal, three-dimensional coordinate axis system having a sensitivity axis, a frequency axis and an epoch axis previously known to be specific for said predetermined body movements being monitored;

three-dimensionally tuning said activity monitor by selectively adjusting amplitude and frequency characteristics of said analog electrical signal in order to remove said irrelevant signal information and to enhance said relevant signal information in order to provide an enhanced signal indicative of said predetermined body movements rather than said general body movements;

affixing said activity monitor onto said patient subject's body, recording said analog electrical signal over a monitoring period by processing said enhanced signal by passing said enhanced signal through a converter means for selectively sampling said tuned, enhanced signal with respect to an appropriate predetermined real time epoch selected according to the type of predetermined body movements being monitored to obtain resultant data signals, if any, which fall within regions defined in said, three-dimensional coordinate axis system which signals are indicative of said predetermined body movements and not of general body movements.

2. The method according to claim 1, wherein said real time epoch is less than said monitoring period.

3. The method according to claim 1, wherein said analog electrical signal is tuned by varying the amplitude characteristics of said analog electrical signal and maintaining the frequency characteristics of said analog electrical signal within a preselected range.

4. The method according to claim 1, wherein said analog electrical signal is tuned by passing a preselected range of amplitudes through said activity monitor while varying the frequency bandpass.

5. The method according to claim 1, wherein said real time epoch is selectively varied over different time periods, all of said different time periods being different from and falling within said monitoring period to obtain resultants for each preselected amplitude and frequency setting which are unique for a particular predetermined body movement.

6. A method of automatically monitoring predetermined body movements of a subject over time by isolating and amplifying said predetermined body movements while ignoring general body movements, said method comprising:

providing an activity monitor capable of producing an analog electrical signal responsive to and characterized by body movements of said subject;

defining within said activity monitor, a mutually orthogonal three-dimensional coordinate axis system having a sensitivity axis, a frequency axis and a real time epoch axis, previously known to be specific for said predetermined body movements being monitored;

affixing the activity monitor to said subject to record body movement data over a preselected subject observation period;

tuning said activity monitor to enhance relevant signal information and to remove irrelevant signal information in order to provide an enhanced signal by selectively adjusting upper and lower threshold frequencies to define a desired frequency bandpass characteristic in said activity monitor so that said analog electrical signal is passed through said frequency bandpass to obtain frequencies indicative of said predetermined body movements and not of said general body movements, by adjusting amplitude characteristics of said analog electrical signal by passing a preselected range of amplitudes through said monitor to define a desired range of amplitudes characteristic of said predetermined body movements, and not of said general body movements and by passing said enhanced signal through a converter means for selectively sampling said enhanced signals with respect to an appropriate real time epoch which is different from and less than said subject observation period to provide resultant data signals, if any, which fall within known activity regions defined in said three-dimensioned coordinate axis system.

7. The method of claim 6, further including selectively varying said real time epoch within said subject observation period to obtain resultant data signals for the amplitude and frequency setting of said activity monitor which are unique for a particular predetermined body movement.

* * * * *